(12) United States Patent
Huang

(10) Patent No.: US 9,046,452 B1
(45) Date of Patent: Jun. 2, 2015

(54) DEVICE AND METHOD FOR LOCATING A FIRST NATURAL BEND OF AN ARROW SHAFT

(71) Applicant: Dorge O. Huang, Henry, IL (US)

(72) Inventor: Dorge O. Huang, Henry, IL (US)

(*) Notice: Subject to any disclaimer, the term of this patent is extended or adjusted under 35 U.S.C. 154(b) by 0 days.

(21) Appl. No.: 14/184,743

(22) Filed: Feb. 20, 2014

(51) Int. Cl.
*G01N 33/46* (2006.01)
*G01N 3/20* (2006.01)
*F42B 35/00* (2006.01)

(52) U.S. Cl.
CPC . *G01N 3/20* (2013.01); *F42B 35/00* (2013.01)

(58) Field of Classification Search
CPC .. G01N 3/20; G01N 33/46; G01N 2203/0023
USPC .......................................................... 73/852
See application file for complete search history.

(56) References Cited

U.S. PATENT DOCUMENTS

| 2,404,584 | A | * | 7/1946 | Liska et al. | 374/52 |
| 3,142,174 | A | * | 7/1964 | Baker | 73/852 |
| 4,662,291 | A | * | 5/1987 | Bardsley | 112/80.41 |
| 6,282,036 | B1 | * | 8/2001 | Woytassek et al. | 359/822 |
| 8,608,531 | B1 | * | 12/2013 | Huang | 451/386 |
| 2009/0040874 | A1 | * | 2/2009 | Rooney et al. | 368/10 |
| 2012/0073383 | A1 | * | 3/2012 | You | 73/847 |
| 2013/0149055 | A1 | * | 6/2013 | Tsai | 408/13 |

FOREIGN PATENT DOCUMENTS

JP 04145216 A * 5/1992 ............. F16C 17/24

OTHER PUBLICATIONS

Printout of www.LanchasterArchery.com illustrating a Ram Arrow Spine Tester.

* cited by examiner

*Primary Examiner* — Lisa Caputo
*Assistant Examiner* — Nathaniel T Woodward
(74) *Attorney, Agent, or Firm* — Donald J. Ersler

(57) ABSTRACT

A device for locating a first natural bend of an arrow shaft preferably includes a support base, two arrow supports, a support tower and a pressure roller unit. The support base includes first and second tracks. The two arrow supports are slidably retained in the first track. Each arrow support includes a pair of bearing wheels for retaining an arrow shaft. The support tower includes a tower base and a tower pedestal. The tower base is slidably retained in the first and second tracks. The pressure roller unit includes a pressure base and two bearing wheels. The pressure base is slidably retained vertically relative to the tower pedestal. The two bearing wheels are sized to receive the arrow shaft. The pressure roller unit is lowered on to the arrow shaft. The arrow shaft is rotated with a forefinger and a thumb to determine the location of a valley.

14 Claims, 6 Drawing Sheets

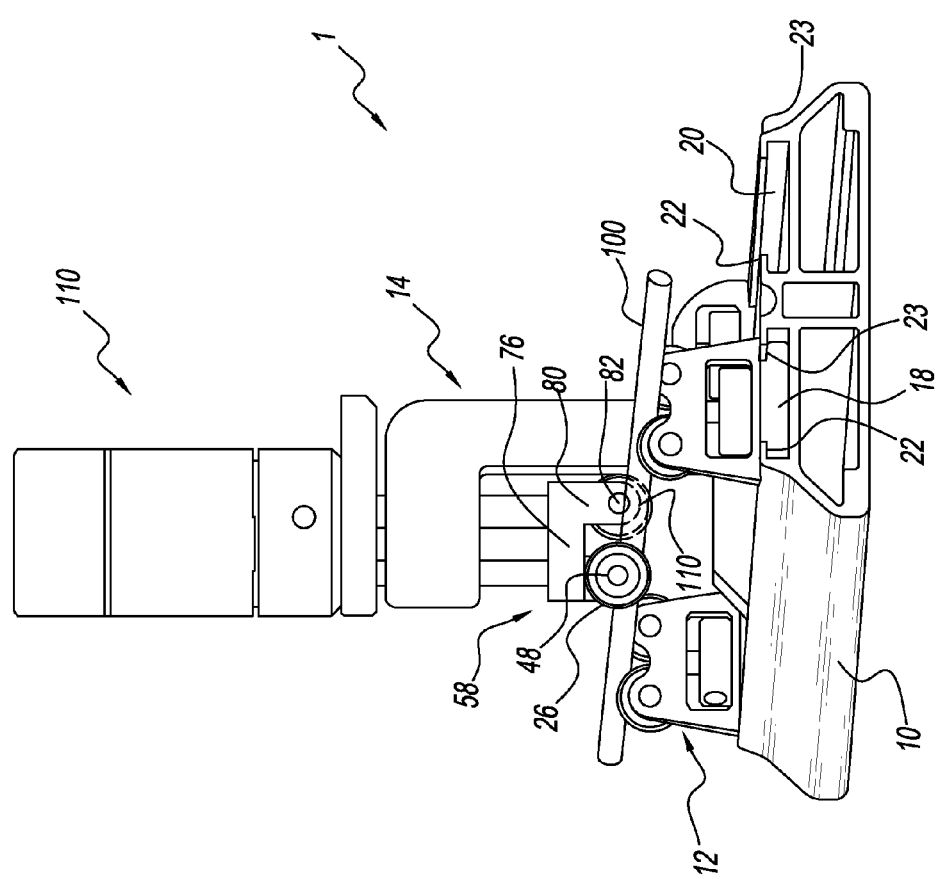

DEVICE AND METHOD FOR LOCATING A FIRST NATURAL BEND OF AN ARROW SHAFT

BACKGROUND OF THE INVENTION

1. Field of the Invention

The present invention relates generally to archery and more specifically to a device and method for locating a first natural bend of an arrow shaft, which allows the first natural bend of the arrow shaft to be located more quickly and accurately than that of the prior art.

2. Discussion of the Prior Art

The prior art discloses at least one first natural bend locator for an arrow shaft. LancasterArchery.com sells a natural bend locator, under the name of Ram Arrow Spine Tester. The Ram Arrow Spine Tester hangs a weight on the arrow shaft to find the first natural bend of the arrow shaft. However, applying weight to an arrow shaft to find the first natural bend stresses the arrow shaft and may not provide the most accurate location of the first natural bend.

Accordingly, there is a clearly felt need in the art for a device and method for locating a first natural bend of an arrow shaft, which does not use a weight to determine the location of the first natural bend.

SUMMARY OF THE INVENTION

The present invention provides a device and method for locating a first natural bend of an arrow shaft, which allows the first natural bend of the arrow shaft to be located more quickly and accurately than that of the prior art. The device for locating a first natural bend of an arrow shaft (arrow bend locating device) preferably includes a support base, two arrow supports, a support tower and a pressure roller unit. The support base preferably includes first and second parallel and adjacent lengthwise tracks. Each track includes a pair of opposing rails. The two arrow supports are slidably retained in the first lengthwise track.

Each arrow support preferably includes a slidable support base, a pair of bearing wheels, an anchor pin and a knurled nut. Each slidable support base includes a pair of opposing rail slots formed in sides thereof to slidably receive the pair of opposing rails of the first track. A nut opening is formed through the slidable support base to provide clearance for the knurled nut. An anchor pin tap is formed through a bottom of the slidable support base to threadably receive a bottom threaded portion of the anchor pin. An anchor hole is formed in a top portion of the slidable support base to rotatably retain a top portion of the anchor pin. The pair of bearing wheels are rotatably retained on a top of the slidable support slidable base to support an arrow shaft. Each roller wheel is preferably crowned to provide tangential contact with the arrow shaft.

The support tower preferably includes a tower base, a tower pedestal, a tower support, at least three sliding rods and a rod plate. The tower base includes a first base portion and a second base portion. The first base portion includes a pair of first opposing rail slots formed in sides thereof to slidably receive the pair of opposing rails of the first track. The second base portion includes a knurled nut, an anchor pin and a pair of second opposing rails slots formed in sides thereof to slidably receive the pair of opposing rails of the second track. A nut opening is formed through the second base portion to provide clearance for the knurled nut. An anchor pin tap is formed through a bottom of the second base portion to threadably receive a bottom threaded portion of the anchor pin. An anchor hole is formed in a top portion of the second base portion to rotatably retain a top portion of the anchor pin.

The tower pedestal extends upward from the tower base. The tower support extends from a top of the tower pedestal. At least three linear bearings are pressed into the tower support to slidably receive the at least three sliding rods. One end of the at least three sliding rods are pressed into the rod plate. The pressure roller unit includes a pressure base and two pressure bearing wheels. The pressure base includes a first wheel projection and a pair of second wheel projections to rotatably retain the two pressure bearing wheels. The other end of the at least three sliding rods are pressed into the pressure base. A measurement indicator may be mounted to the tower pedestal, such that an indicator tip of the measurement indicator contacts an edge of the rod plate.

A vibration module preferably includes a vibration housing and a vibration unit. The vibration housing includes a mounting base a modular column and a top cap. The mounting base includes a threaded stud, which extends from a bottom of thereof. The threaded stud is screwed into the rod plate to retain the vibration module. Each end of the outer perimeter of the modular column is threaded to threadably receive inner perimeter threads formed in the mounting base and the top cap. The vibration unit preferably includes a vibration motor, a digital timer, a momentary switch and a power source. The digital timer is started by depressing the momentary switch. The digital timer supplies power from the power source to the vibration motor for a set period of time. The digital timer and vibration motor are preferably retained in the mounting base. The power source may secured to an inside perimeter of the modular column. The momentary switch is preferably located in a side wall of the mounting base. The vibration module is used to effectively float the arrow shaft relative to the bearing wheels and thus reduce friction between the same.

The arrow bend locating device is preferably used in the following manner. The two arrow supports are adjusted on the support base to support each end of an arrow shaft. The arrow shaft is placed in the arrow shaft supports. The pressure roller unit is lowered on to the arrow shaft. The arrow shaft is rotated on an end with a forefinger and a thumb. The arrow shaft will normally have three or four valleys. The valley that has the strongest "snapping" feedback is the first natural bend.

Accordingly, there is a clearly felt need in the art for an arrow bend locating device, which does not use a weight to determine the location of the first natural bend.

Finally, it is another object of the present invention to provide an arrow bend locating device, which allows the first natural bend of the arrow shaft to be located more quickly and accurately than that of the prior art.

These and additional objects, advantages, features and benefits of the present invention will become apparent from the following specification.

BRIEF DESCRIPTION OF THE DRAWINGS

FIG. 4 is a perspective end view of an arrow shaft retained in an arrow bend locating device in accordance with the present invention.

DETAILED DESCRIPTION OF THE PREFERRED EMBODIMENTS

Figure 1:
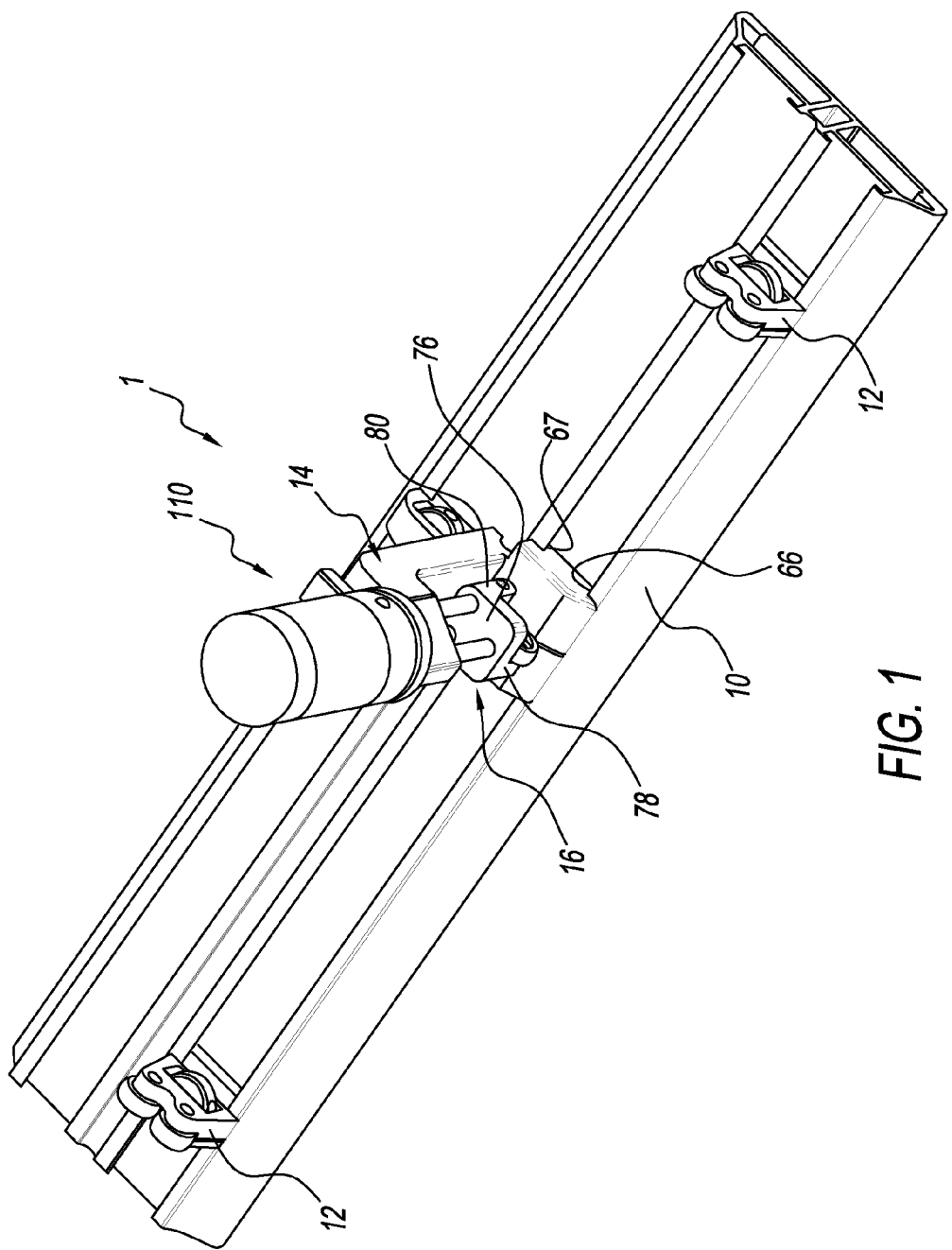
FIG. 1 is a top perspective view of an arrow bend locating device in accordance with the present invention.
Figure 2:
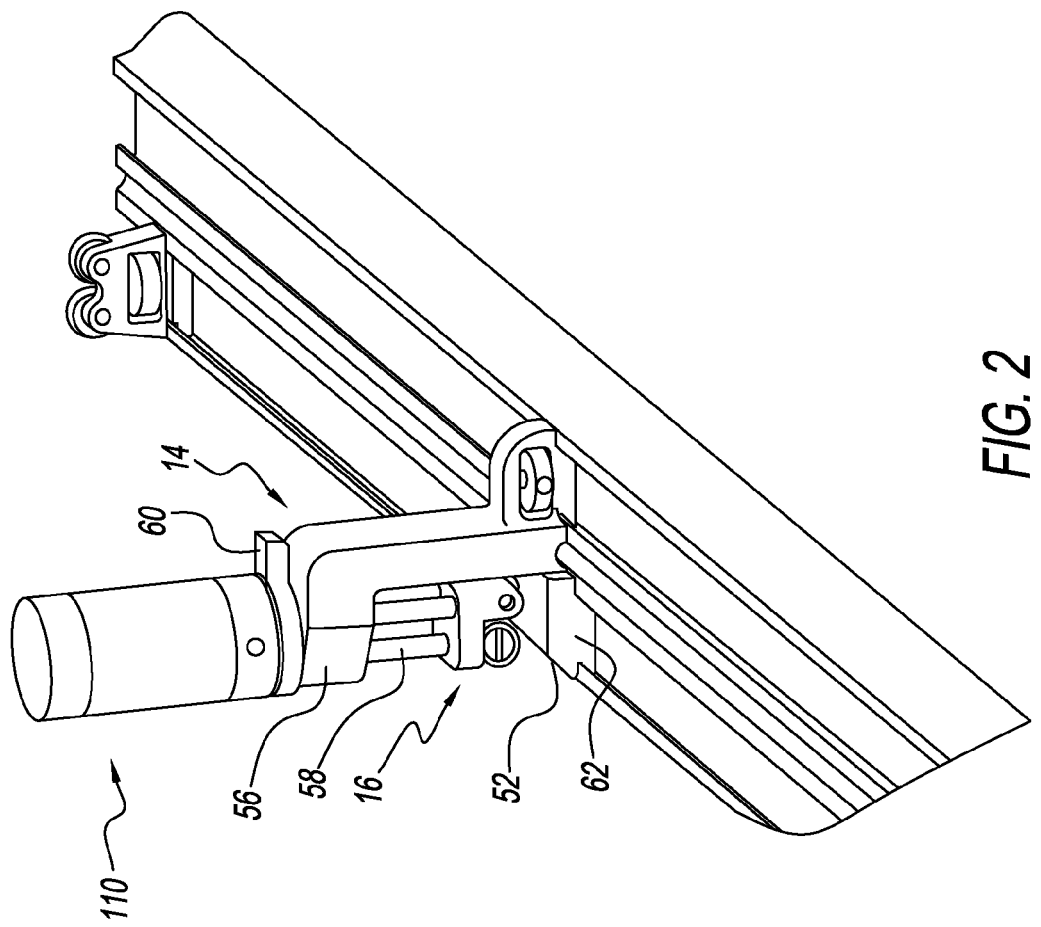
FIG. 2 is a partial end perspective view of an arrow bend locating device in accordance with the present invention.
Figure 3:
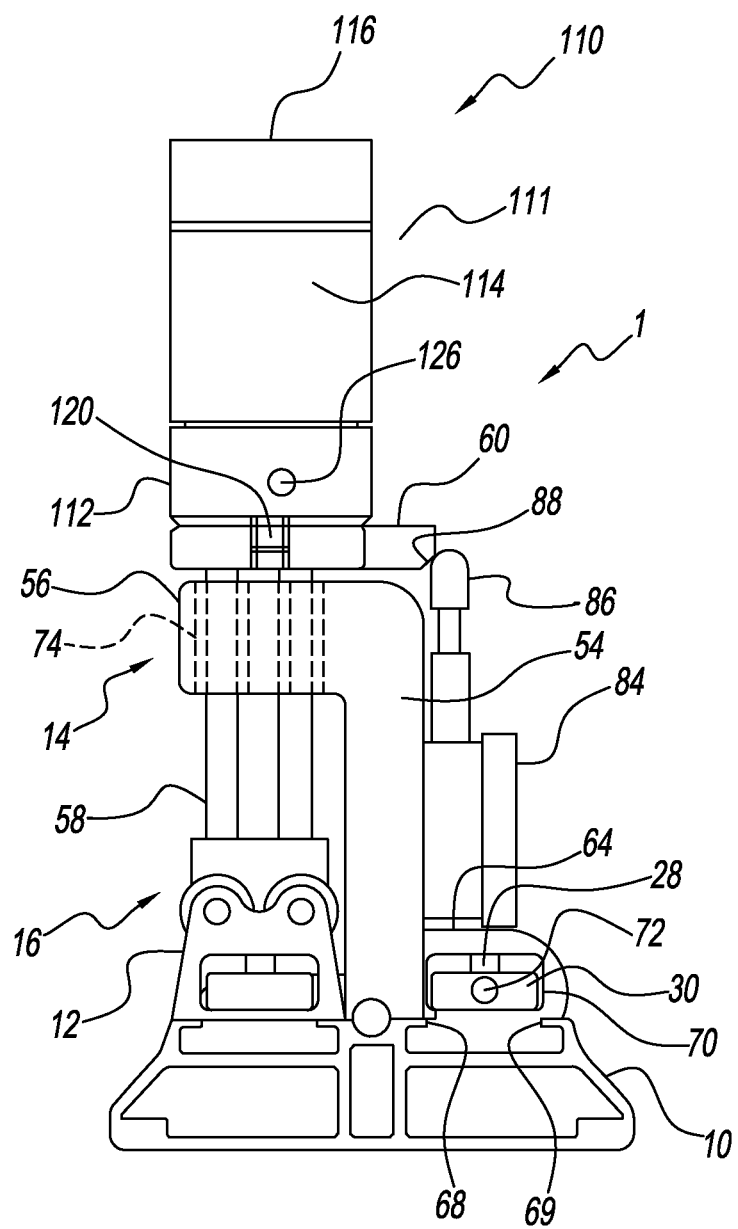
FIG. 3 is an end view of an arrow bend locating device in accordance with the present invention.

With reference now to the drawings, and particularly to FIG. 1, there is shown a perspective view of an arrow bend locating device 1. With reference to FIGS. 2-4, the arrow bend locating device 1 preferably includes a support base 10, two arrow supports 12 and a support tower 14 and a pressure roller unit 16. The support base 10 preferably includes a first track 18 and a second track 20, which are parallel and adjacent to each other. Each track 18, 20 includes a pair of opposing rails 22, 23. The two arrow supports 12 are slidably retained in the first lengthwise track 18.

Figure 5:
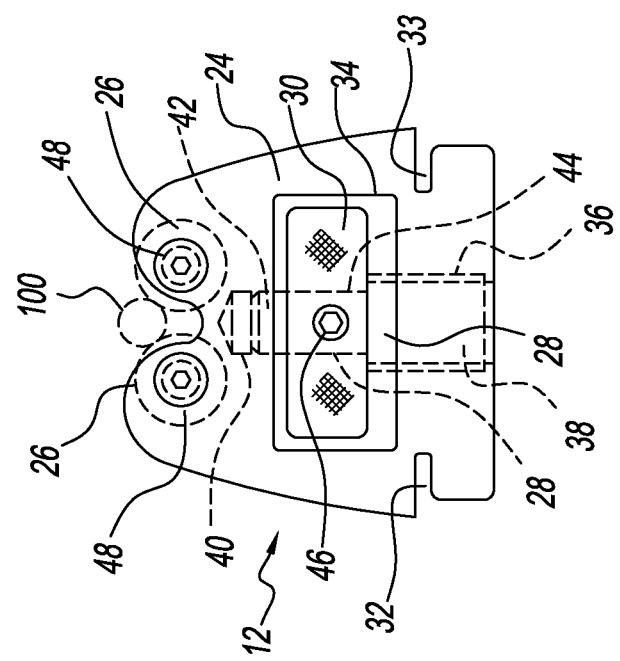
FIG. 5 is an end view of an arrow support of an arrow bend locating device in accordance with the present invention.

With reference to FIG. 5, each arrow support 12 preferably includes a slidable support base 24, a pair of bearing wheels 26, an anchor pin 28 and a knurled nut 30. Each slidable support base 24 includes a pair of opposing rail slots 32, 33 formed in sides thereof to slidably receive the pair of opposing rails 22, 23 of the first track 18. A nut opening 34 is formed through the slidable support base 24 to provide clearance for the knurled nut 30. An anchor pin tap 36 is formed through a bottom of the slidable support base 24 to threadably receive a bottom threaded portion 38 of the anchor pin 28. An anchor hole 40 is formed in a top portion of the slidable support base 24 to rotatably retain a top portion 42 of the anchor pin 28.

The knurled nut 30 includes an anchor pin hole 44 to receive the top portion 42 of the anchor pin 28. A set screw tap is formed through the knurled nut 30 perpendicular to the anchor pin hole 44. A set screw 46 is threadably engaged in the set screw tap. The set screw 46 is tightened against the top portion 42, such that the knurled nut 30 is used to rotate the anchor pin 28. However, other devices or methods besides the anchor pin 28 and the knurled nut 30 may also be used for anchoring a position of the two arrow supports 12 relative to the support base 10.

Figure 6:
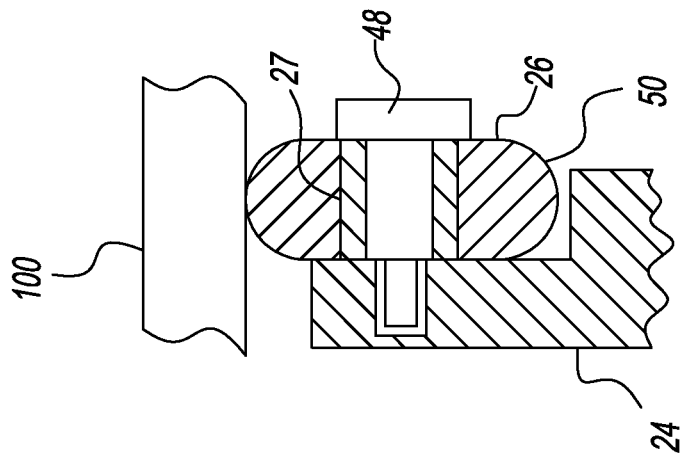
FIG. 6 is an enlarged side view portion of a bearing wheel retained on an arrow support of an arrow bend locating device in accordance with the present invention.

The pair of bearing wheels 26 are preferably rotatably retained in the top of the slidable support base 24 with a pair of shoulder bolts 48. The shoulder bolts 48 are preferably fabricated from brass to ensure smooth rotation of the pair of roller wheels 26. With reference to FIG. 6, a brass bearing 27 is preferably pressed into each bearing wheel 26 to rotatably receive the shoulder bolt 48. The pair of roller wheels 26 are preferably positioned, such that an arrow shaft 100 is substantially centered relative to a profile of the slidable support base 24. Each bearing wheel 26 preferably includes a crowned profile 50. The crowned profile 50 provides tangential contact with the arrow shaft 100.

The support tower 14 includes a tower base 52, a tower pedestal 54, a tower support 56, at least three sliding rods 58 and a rod plate 60. The tower base 52 includes a first base portion 62 and a second base portion 64. The first base portion 62 includes a pair of first opposing rail slots 66, 67 formed in opposing sides thereof to slidably receive the pair of opposing rails 22, 23 of the first track 18. The second base portion 64 includes the anchor pin 28, the knurled nut 30 and a pair of second opposing rails slots 68, 69 formed in opposing sides thereof to slidably receive the pair of opposing rails 22, 23 of the second track 20. A nut opening 70 is formed through the second base portion 64 to provide clearance for the knurled nut 30. An anchor pin tap is formed through a bottom of the second base portion 64 to threadably receive a bottom threaded portion 36 of the anchor pin 28. An anchor hole is formed in a top portion of the second base portion 64 to rotatably retain a top portion of the anchor pin 28. A set screw 72 is used to engage the knurled nut 30 with the anchor pin 28. Rotation of the knurled nut 30 secures the support tower 14 relative to the support base 10.

The tower pedestal 54 extends upward from the tower base 52. The tower support 56 extends from a top of the tower pedestal 54. At least three linear bearings 74 are pressed into the tower support to slidably receive the at least three sliding rods 58. The linear bearings 74 preferably extend substantially a thickness of the tower support 56. One end of the at least three sliding rods 58 are pressed into the rod plate 60. The pressure roller unit 16 includes a pressure base 76 and the two bearing wheels 26. The pressure base 76 includes a first wheel projection 78 and a pair of second wheel projections 80. The other end of the at least three sliding rods 58 are pressed into the pressure base 76. A first one of the two bearing wheels 26 is rotatably retained on the first wheel projection 78 with the shoulder screw 48. A second one of the two bearing wheels 26 is rotatably retained between the pair of second wheel projections 80 with a wheel pin 82. With reference to FIG. 3, a measurement indicator 84 may be mounted to the tower pedestal 54, such that an indicator tip 86 contacts a chambered edge 88 of the rod plate 60.

Figure 7:
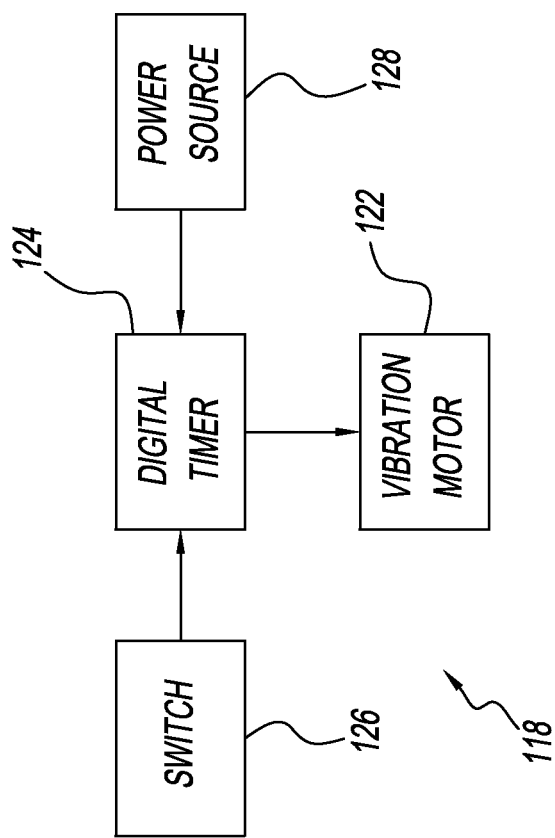
FIG. 7 is a schematic diagram of a vibration module of an arrow bend locating device in accordance with the present invention.

With reference to FIG. 7, a vibration module 110 preferably includes a vibration housing 111 and a vibration unit 118. The vibration housing includes a mounting base 112, a modular column 114 and a top cap 116. The mounting base 112 includes a threaded stud 120 extending from a bottom thereof. The threaded stud 120 is screwed into the rod plate 60 to retain the vibration module 110. Each end of the outer perimeter of the modular column 114 is threaded to threadably receive inner perimeter threads formed in the mounting base 112 and the top cap 116 (not shown). The vibration unit 118 includes a vibration motor 122, a digital timer 124, a momentary switch 126 and a power source 128. The digital timer 124 is started by depressing the momentary switch 126. The digital timer 124 supplies power from the power source 128 to vibration motor 122 for a set period of time. The digital timer 124 and the vibration motor 122 are preferably retained in the mounting base 112. The power source 128 may secured to an inside perimeter of the modular column 114. The momentary switch 126 is preferably located in a side wall of the mounting base 112. The vibration module 110 is used to effectively float the arrow shaft 100 relative to the roller wheels 26 and thus reduce friction between the same.

The arrow bend locating device 1 is preferably used in the following manner. The two arrow supports 12 are adjusted on the support base 10 to support each end of the arrow shaft 100. The arrow shaft 100 is placed in the arrow shaft supports 12. The pressure roller unit 16 is lowered on to the arrow shaft 100. The arrow shaft 100 is rotated on an end with a forefinger and a thumb. The arrow shaft 100 will normally have three or four valleys. The valley that has the strongest "snapping" feedback is the first natural bend.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

I claim:

1. A device for locating a first natural bend of an arrow shaft comprising:

a support base having a first end and a second end, said support base having a first track and a second track, each one of said first and second tracks including a pair of inward facing rails;

a first arrow support is located at said first end of said support base in said first track, said first arrow support includes a first pair of bearing wheels for supporting said arrow shaft;

a second arrow support is located at said second end of said support base in said first track, said second arrow support includes a second pair of bearing wheels for supporting said arrow shaft;

a support tower includes a tower base, a tower pedestal and a tower support, said tower base is retained in said first and second tracks, said tower pedestal extends upward from said tower base, said tower support extends from said tower pedestal; and a pressure roller unit extends downward from said tower support, said pressure roller unit includes a pressure pair of bearing wheels, wherein said pressure unit is lowered to place said pressure pair of bearing wheels in contact with the arrow shaft, an end of the arrow shaft is turned to determine a location of at least one bend; and a vibration unit in contact with said pressure roller, wherein said vibration unit cases said pressure roller to vibrate, said vibration unit effectively floats said arrow shaft relative to said bearing wheels and thus reduces friction therebetween.

2. The device for locating a first natural bend of said arrow shaft of claim 1 wherein:

said first and second pair of bearing wheels include a crowned profile.

3. The device for locating a first natural bend of said arrow shaft of claim 1, further comprising:

said support tower includes at least one sliding rod and a rod plate, said tower base is located between said first and second arrow supports, said at least one sliding rod is slidably retained in said tower support, one end of said at least one sliding rod is retained in said rod plate, said pressure unit is retained on the other end of said at least one sliding rod.

4. The device for locating a first natural bend of said arrow shaft of claim 3 wherein:

said first arrow support, said second arrow support and said support tower each include a device for anchoring to said support base.

5. The device for locating a first natural bend of said arrow shaft of claim 3, further comprising:

a measurement indicator attached to said tower pedestal, an indicator tip of said measure indicator in contact with said rod plate.

6. The device for locating a first natural bend of said arrow shaft of claim 3, further comprising:

said vibration unit including a vibration motor, a digital timer and a power source, where said digital timer is activated to provide a supply of electrical power from said power source to said vibration motor.

7. The device for locating a first natural bend of said arrow shaft of claim 6, further comprising:

said vibration unit is contained in a vibration housing, said vibration housing is secured to said support tower.

8. The device for locating a first natural bend of said arrow shaft of claim 1, further comprising:

said support tower includes at least three sliding rods and a rod plate, said tower base is located between said first and second arrow supports, said at least one sliding rod is slidably retained in said tower support, one end of said at least one sliding rod is retained in said rod plate, said pressure unit is retained on the other end of said at least one sliding rod.

9. A device for locating a first natural bend of an arrow shaft comprising:

a support base having a first end and a second end, said support base having a first track and a second track, each one of said first and second tracks including a pair of inward facing rails;

a first arrow support is located at said first end of said support base in said first track, said first arrow support includes a first pair of bearing wheels for supporting said arrow shaft;

a second arrow support is located at said second end of said support base in said first track, said second arrow support includes a second pair of bearing wheels for supporting said arrow shaft;

a support tower includes a tower base, a tower pedestal and a tower support, said tower base is retained in said first and second tracks, said tower pedestal extends upward from said tower base, said tower support extends from said tower pedestal, said inward facing rails of said first and second tracks are slidably engaged with said tower base; and a pressure roller unit extends downward from said tower support, said pressure roller unit includes a pressure pair of bearing wheels, wherein said pressure unit is lowered to place said pressure pair of bearing wheels in contact with the arrow shaft, an end of the arrow shaft is turned to determine a location of at least one bend; and a vibration unit including a vibration motor, a digital timer and a power source, wherein said digital timer is activated to provide a supply of electrical power from said power source to said vibration motor to vibrate bearing wheels of said pressure roller.

10. The device for locating a first natural bend of said arrow shaft of claim 9 wherein:

said first and second pair of bearing wheels include a crowned profile.

11. The device for locating a first natural bend of said arrow shaft of claim 9, further comprising:

said support tower includes at least one sliding rod and a rod plate, said tower base is located between said first and second arrow supports, said at least one sliding rod is slidably retained in said tower support, one end of said at least one sliding rod is retained in said rod plate, said pressure unit is retained on the other end of said at least one sliding rod.

12. The device for locating a first natural bend of said arrow shaft of claim 11 wherein:

said first arrow support, said second arrow support and said support tower each include a device for anchoring to said support base.

13. The device for locating a first natural bend of said arrow shaft of claim 11, further comprising:

a measurement indicator attached to said tower pedestal, an indicator tip of said measure indicator is in contact with said rod plate.

14. The device for locating a first natural bend of said arrow shaft of claim 9, further comprising:

said support tower includes at least three sliding rods and a rod plate, said tower base is located between said first and second arrow supports, said at least one sliding rod is slidably retained in said tower support, one end of said at least one sliding rod is retained in said rod plate, said pressure unit is retained on the other end of said at least one sliding rod.

\* \* \* \* \*